United States Patent [19]
Yasue et al.

[11] Patent Number: 5,477,732
[45] Date of Patent: Dec. 26, 1995

[54] ADHESION MEASURING METHOD

[75] Inventors: Takao Yasue; Tadashi Nishioka, both of Itami, Japan

[73] Assignees: Mitsubishi Denki Kabushiki Kaisha, Tokyo; Ryoden Semiconductor System Engineering Corporation, Hyogo, both of Japan

[21] Appl. No.: 314,962

[22] Filed: Sep. 29, 1994

[30]    Foreign Application Priority Data

Oct. 18, 1993 [JP] Japan .................................... 5-259869

[51] Int. Cl.$^6$ ................................................ G01B 21/30
[52] U.S. Cl. ................................................ 73/105
[58] Field of Search ............................ 73/105; 250/306, 250/307

[56]             References Cited
        U.S. PATENT DOCUMENTS

| 5,193,383 | 3/1993 | Burnham et al. | 250/307 |
| 5,237,859 | 8/1993 | Elings et al. | 250/306 |
| 5,308,974 | 5/1994 | Elings et al. | 250/306 |
| 5,329,808 | 7/1994 | Elings et al. | 250/307 |
| 5,363,697 | 11/1994 | Nakagawa | 250/306 |
| 5,372,930 | 12/1994 | Colton et al. | 250/306 |

FOREIGN PATENT DOCUMENTS 241777  9/1994  Japan ...................................... 73/105

OTHER PUBLICATIONS

Burenham et al., "Measuring the Nanomechanical Properties and Surface Forces of Materials Using an Atomic Force Microscope", Journal of Vac. Sci. Technology, vol. A7, No. 4, Jul./Aug. 1989, pp. 2906–2913.

Nakagawa et al, "Discriminating Molecular Length of Chemically Adsorbed Molecules Using An Atomic Force Microscope Having A Tip Covered With Sensor Molecules (An Atomic Force Microscope Having Chemical Sensing Function)", Japanese Journal of Applied Physics, vol. 32, Part 2, No. 2B, Feb. 1993, pp. L294–L296.

Primary Examiner—Hezron E. Williams
Assistant Examiner—Daniel S. Larkin
Attorney, Agent, or Firm—Leydig, Voit & Mayer

[57]              ABSTRACT

An adhesion measuring apparatus includes a measuring device for measuring a Force-Curve at each of multiple measuring points on a sample surface using a cantilever provided at its distal end with a probe which is made of a material to be formed on the sample surface, and a distribution image forming device for calculating adhesion between a material making up the sample surface and the material to be formed on the sample surface from an output of the measuring device, and forming an image of adhesion distribution on the sample surface. An adhesion measuring method includes the steps of adjusting the spacing between a probe which is provided at the distal end of a cantilever and made of a material to be formed on a sample surface and the sample surface to measure a Force-Curve at each of multiple measuring points on the sample surface, calculating adhesion between a material making up the sample surface and the material to be formed on the sample surface at each of the measuring points from the result of measuring the Force-Curve, and forming an image of adhesion distribution on the sample surface from the adhesion calculated for each of the measuring points. With the present adhesion measuring apparatus and method, the condition of the sample surface can be accurately determined at an atomic level.

7 Claims, 17 Drawing Sheets

ADHESION MEASURING METHOD

BACKGROUND OF THE INVENTION

1. Field Of The Invention

The present invention relates to an adhesion measuring apparatus and method for measuring an adhesive force of a sample surface. The present invention also relates to a semiconductor device manufacturing method using the adhesion measuring method.

2. Description of the Related Art

FIG. 20 shows a conventional interatomic force microscope. A laser beam emitted from a semiconductor laser unit 4 is focused on an upper surface of a cantilever 1, and a reflected beam from the cantilever 1 enters a photodiode detector 5. The photodiode detector 5 detects a shift in position of the reflected beam from the cantilever 1, thereby determining a minute flexure of the cantilever 1 due to the interatomic force acting between a probe 2 provided at the distal end of the cantilever 1 and a sample 3 to be measured.

A description will now be made of operation of measuring an image of surface irregularities of the measured sample 3 by such an interatomic force microscope. First, a voltage is applied to a Z-electrode of a cylindrical piezoelectric element 6 by a controller 7 to perform feedback control while moving the measured sample 3 in the Z-direction (i.e., vertically) so that the reflected beam from the cantilever 1 enters a fixed position on the photodiode detector 5. While the cylindrical piezoelectric element 6 is thus actuated in the Z-direction under feedback control, voltages are applied to X- and Y-electrodes of the cylindrical piezoelectric element 6 by a computer 8 through the controller 7 so as to scan the measured sample 3 in the X- and Y-directions simultaneously. By reading the respective voltages in the X-, Y- and Z-directions applied from the controller 7 to the cylindrical piezoelectric element 6, an image of the sample surface can be produced.

As described in Japanese Patent Application No. 5-26841 previously filed, the inventor has proposed a method of measuring surface adhesion of the measured sample 3 using the interatomic force microscope shown in FIG. 20. The term "surface adhesion" employed herein means an adhesive force between a material making up the sample surface and a material to be formed on the sample surface. The surface adhesion is measured by, for example, moving the measured sample 3 vertically to change the surface position of the measured sample 3 relative to the probe 2, and determining a flexure of the cantilever 1 with respect to a Z-directional displacement of the measured sample 3 at this time. The flexure of the cantilever 1 with respect to the Z-directional displacement of the measured sample 3 is measured by the photodiode detector 5 as a shift of the position where the laser beam reflected by the cantilever 1 enters the photodiode detector 5.

More specifically, the surface adhesion is measured in accordance with sequential steps S1 to S7 below.

S1: First, the probe 2 is moved to one measuring point on the measured sample 3.

S2: Assume here that an output voltage of the photodiode detector 5 is Vd and an arbitrary set voltage is Vs. A stepping motor (not shown) for moving the cylindrical piezoelectric element 6 in the Z-direction is actuated so that the measured sample 3 comes closer to the probe 2 of the cantilever 1.

S3: When the measured sample 3 reaches a position near the probe 2, a voltage is applied to the piezoelectric element 6 by the controller 7 to move the piezoelectric element 6 in the Z-direction, making the measured sample 3 come further closer to the probe 2. This produces an interatomic force acting between the measured sample 3 and the probe 2 to flex the cantilever 1. The incident position of the laser beam on the photodiode detector 5 is thereby shifted, whereupon the output voltage Vd of the photodiode detector 5 is varied. When the offset voltage represented by the sum Vd+Vs of the output voltage Vd and the set voltage Vs becomes 0, a feedback circuit in the controller 7 is turned on to apply a voltage Vz to the Z-electrode of the piezoelectric element 6 from the controller 7 for automatic control so that the offset voltage is maintained at 0. The voltage Vz applied in such a feedback position is assumed to be Vc.

S4: The feedback circuit in the controller 7 is turned off.

S5: A triangular wave of ±160 V with the applied voltage Vc at the center is additionally applied to the Z-electrode of the piezoelectric element 6 to move the measured sample 3 up and down in the Z-direction. The flexure of the cantilever 1 with respect to the Z-directional displacement of the measured sample 3 at this time measured by the photodiode detector 5 is read from an output voltage value of the photodiode detector 5. Graphic representation of the dependency of the offset voltage Vd+Vs upon the voltage Vz applied to the piezoelectric element is called a Force-Curve.

S6: The feedback circuit in the controller 7 is turned on again for moving the measured sample 3 in the Z-direction to the original feedback position.

S7: The above steps S1 to S6 are repeated several times for one measuring point.

The Force-Curve obtained as described above is shown in FIG. 21. Conditions of the cantilever 4 in points A to G on the Force-Curve of FIG. 21 are shown in FIGS. 22A to 22G, respectively. In FIG. 21, the vertical axis represents the offset voltage Vd+Vs, i.e., the force acting between the probe 2 and the measured sample 3. At a certain position in the direction of the vertical axis, F=0. A repulsion is produced in a region on the positive side in the direction of the vertical axis from F=0, whereas an attraction is produced in a region on the negative side in the direction of the vertical axis from F=0. The larger the distance from the straight line indicative of F=0, the stronger will be either force. On the other hand, horizontal axis represents the voltage Vz applied to the Z-electrode of the cylindrical piezoelectric element 6. The measured sample 3 and the probe 2 of the cantilever 1 come closer to each other with a point on the curve moving toward the left in FIG. 21.

First, at the point A on the straight line of F=0, no forces act between the cantilever 1 and the measured sample 3 as shown in FIG. 22A. When the voltage Vz applied to the piezoelectric element 16 is gradually increased to make the sample 3 come closer to the cantilever 1, an attraction abruptly acts on the cantilever 1 at the point B in FIG. 21 because the probe 2 absorbs a layer of contaminants such as moisture on the surface of the sample 3, i.e., a so-called contaminant layer 3a. Therefore, the probe 2 of the cantilever 1 comes to a position closest to the sample 3 as shown in FIG. 22B. When the sample 3 is further raised in the Z-direction, the attraction acting between the probe 2 and the sample 3 is diminished, resulting in F=0 at the point C. After that, a repulsion acts between the probe 2 and the sample 3. Thus, the warping of the cantilever 1 is canceled at the point C as shown in FIG. 22C, and the cantilever 1 is then curved in the direction of parting the probe 2 from the sample 3 at the point D as shown in FIG. 22D.

Under the above condition, when the voltage Vz applied to the piezoelectric element 16 is now gradually reduced to displace the sample 3 farther away from the cantilever 1, the repulsion is also diminished correspondingly, resulting in F=0 at the point E where the warping of the cantilever 1 is canceled, as shown in FIG. 22E. When the sample 3 is displaced even farther away from the probe 2, an attraction acts between the two members. The attraction is gradually increased, causing the cantilever 1 to warp toward the sample 3 as shown in FIG. 22F. Reaching the point F, however, there occurs an abrupt jump from the attraction region to the point G, whereupon the probe 2 of the cantilever 1 is detached from the contaminant layer 3a of the sample 3 so that the cantilever 1 takes a linear shape substantially free from any warping, as shown in FIG. 22G.

The surface adhesion between the sample 3 and the probe 2 is measured quantitatively from the following equation based on the flexure of the cantilever 1 which corresponds to the variation $\Delta V_z$ in the voltage $V_z$ applied to the piezoelectric element 6 between the point E indicative of F=0 and the point F in the Force-Curve obtained as above:

Surface adhesion=spring constant×flexure of the cantilever

Because the Force-Curve represents the interatomic force acting between atoms in the surface of the probe 2 and atoms in the surface of the measured sample 3, the resulting Force-Curve is different depending on materials of the probe 2 or the measured sample 3. In Jpn. J. Appl. Phys., Vol. 32 (1993) L295, for example, two typical Force-Curves C1 and C2 measured by using the conventional interatomic force microscope are depicted as shown in FIG. 23. These Force-Curves C1 and C2 are obtained by measuring the same sample surface using two probes whose surfaces are made of different materials from each other. It is seen that the surface adhesion between the sample and the probe varies depending on the difference in material of the probe surface even with the sample being the same.

As described above, it has been proposed in Japanese Patent Application No. 5-26841, now Japanese Published Document No. 6-241777 to determine the surface adhesion between a probe and a measured sample from measurement of the Force-Curve. But while the specific purpose of the interatomic force microscope is to produce an image of surface irregularities for determining three-dimensionally, the shape of the sample surface, the surface adhesion is only considered as a physical quantity that is determined depending on a material of the sample surface and a material of the probe. Accordingly, it has heretofore been just proposed to measure the Force-Curve at one arbitrary point on the measured sample surface, thereby determining the surface adhesion.

However, when a multilayer structure is formed through a number of processes as needed in, for example, general semiconductor devices, residual particles due to the preceding process sometimes exist on the surface of a certain layer. In such a case, with an image of surface irregularities, the shape of the layer surface can be determined, but whether foreign matter of different constituent elements exist on the surface cannot be confirmed. Also, the surface adhesion is different between areas where residual particles are present in areas where no residual particles are present because of the different in constituent elements. Accordingly, there is a fear that an accurate adhesion force may not be obtained from a measurement made at only one point.

Thus, the interatomic force microscope and the adhesion measuring method in the prior art have difficulties in accurately determining the condition of the sample surface at an atomic level.

SUMMARY OF THE INVENTION

The present invention has been made to solve the above problem in the prior art, and its object is to provide an adhesion measuring apparatus and method by which the condition of the sample surface can be accurately determined at an atomic level.

Another object of the present invention is to provide a semiconductor device manufacturing method using the adhesion measuring method.

An adhesion measuring apparatus according to the present invention comprises:

measuring means for measuring a Force-Curve at each of a plurality of measuring points on a sample surface by using a cantilever provided at its distal end with a probe which is made of a material to be formed on the sample surface, and distribution image forming means for calculating adhesion between a material making up the sample surface and the material to be formed on the sample surface from an output of the measuring means, and forming an image of adhesion distribution on the sample surface.

The adhesion measuring method according to the present invention comprises the steps of:

adjusting a spacing between a probe which is provided at the distal end of a cantilever and is made of a material to be formed on a sample surface and the sample surface to thereby measure a Force-Curve at each of a plurality of measuring points on the sample surface, calculating an adhesion between a material making up the sample surface and the material to be formed on the sample surface at each of the measuring points from the result of measuring the Force-Curve, and forming an image of adhesion distribution on the sample surface from the adhesion calculated fox each of the measuring points.

Further, the semiconductor device manufacturing method according to the present invention comprises:

an inspection step of measuring an adhesion between the surface of one of a substrate, an insulating film, a wiring layer, an electrode layer and a resist layer making up a semiconductor device and a second material to be formed on the surface of the first material, and measuring an image of adhesion distribution as well, and a step of forming the second material on the surface of the first material when it is determined in the inspection step that the measured adhesion is greater than a predetermined value.

DESCRIPTION OF THE PREFERRED EMBODIMENTS

Embodiment 1

Figure 1:
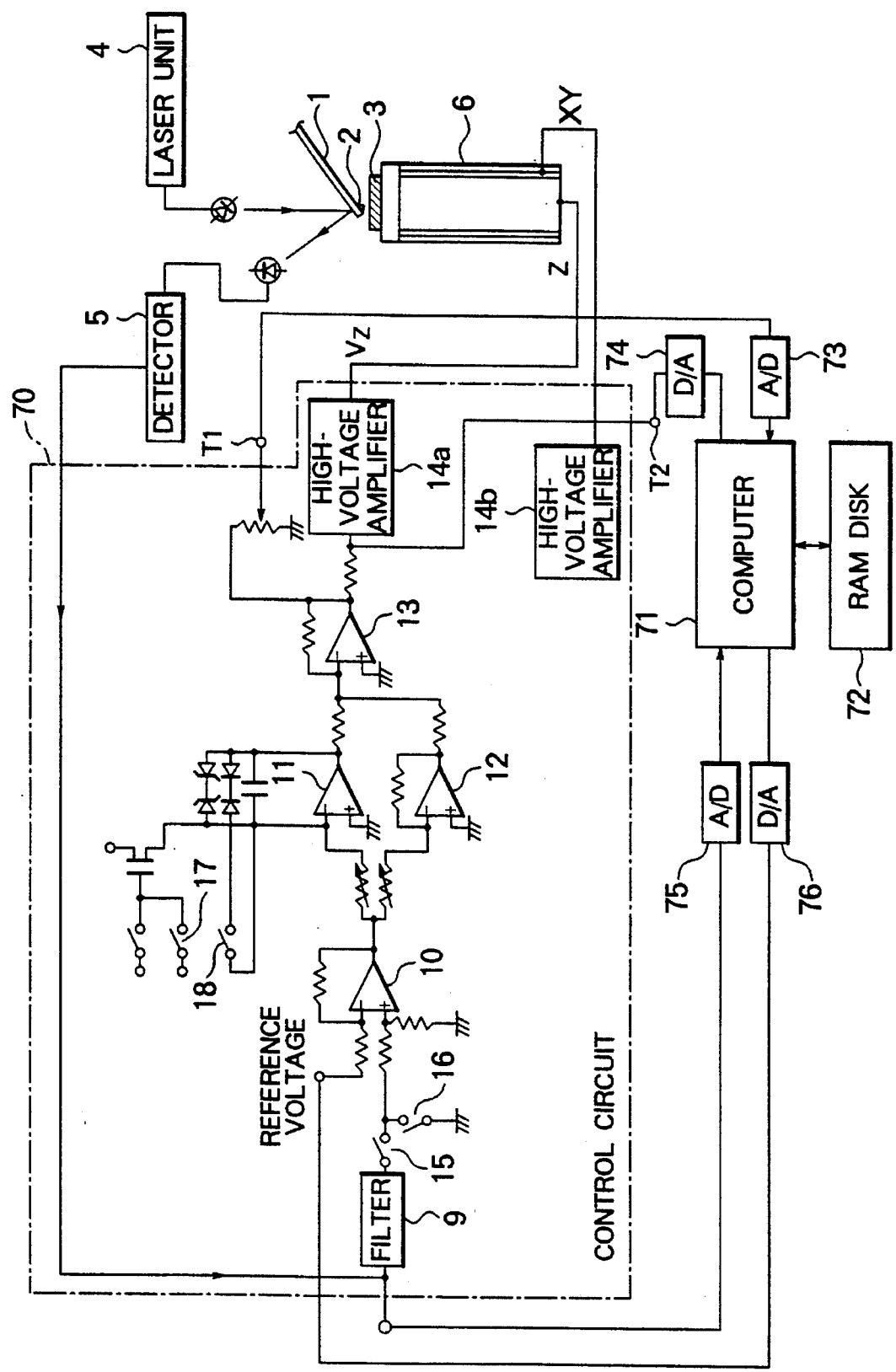
FIG. 1 is a diagram of an adhesion measuring apparatus according to Embodiment 1 of the present invention.

FIG. 1 shows an arrangement of an adhesion measuring apparatus according to Embodiment 1 of the present invention. A cantilever 1 is disposed below a semiconductor laser unit 4, and a cylindrical piezoelectric element 6 is disposed below the cantilever 1. A photodiode detector 5 is disposed above the cantilever 1, and a control circuit 70 for scanning the piezoelectric element 6 in the X-, Y- and Z-directions is connected to the photodiode detector 5. Also, a computer 71 is connected to the control circuit 70 through A/D converters 73 and 75 and D/A converters 74, 76, and a RAM disk 72 is connected to the computer 71. Attached to the distal end of the cantilever 1 is a probe 2 made of a material which is to be formed on the surface of a sample and of which an adhesion to the sample surface is to be measured.

The control circuit 70 includes a filter 9 connected to an output of the photodiode detector 5. A differential amplifier 10 is connected to the filter 9 through switches 15 and 16. Further, an integrating amplification circuit 11 and a proportional amplification circuit 12 are connected to the differential amplifier 10 in parallel, and an adder 13 is connected to outputs of these amplification circuits 11 and 12. An output of the adder 13 is connected to an AFM (interatomic force microscope) image signal output terminal T1 and also to a Z-electrode of the piezoelectric element 6 through a high-voltage amplifier 14a. Connected to the input side of the high-voltage amplifier 14a is an input terminal T2 via which a Z-driving triangular wave voltage is applied from the computer 71 through the D/A converter 74. The control circuit 70 further includes a high-voltage amplifier 14b for applying X- and Y-scan voltages to X- and Y-electrodes of the piezoelectric element 6, respectively, in accordance with commands from the computer 71.

Operation of the above adhesion measuring apparatus for measuring image data of surface irregularities is basically similar to operation of the conventional interatomic force microscope described above. First, in FIG. 1, the switch 15 is closed and the switch 16 is opened in the control circuit 70. A laser beam emitted from the semiconductor laser unit 4 irradiates an upper surface of the cantilever 1, and a reflected beam from the cantilever 1 enters the photodiode detector 5. The photodiode detector 5 detects a shift in position of the reflected beam from the cantilever 1, thereby determining a minute flexure of the cantilever 1 due to the interatomic force acting between a sample 3 to be measured which is held on the piezoelectric element 6 and a probe 2 which is provided at the distal end of the cantilever 1. An output signal of the photodiode detector 5 is transmitted to the differential amplifier 10 through the filter 9 in the control circuit 70, and is compared there with a reference voltage that is supplied to the differential amplifier 10 from the computer 71 through the D/A converter 76. An output of the differential amplifier 10 is amplified by the integrating amplification circuit 11 and the proportional amplification circuit 12, and respective outputs of these amplification circuits are added by the subsequent adder 13. An output of the adder 13 is further increased in its voltage by the high-voltage amplifier 14a, and the resulting signal is applied as a Z-directional control voltage to the Z-electrode of the cylindrical piezoelectric element 6. A feedback loop is thus formed.

Through the above feedback loop, the Z-directional position of the sample 3 is subject to feedback control so that an output level of the photodiode detector 5 is kept constant. Data concerning irregularities (AMF image) are taken into the computer 71 through the A/D converter 73 from the output terminal T1 connected to the output side of the adder 13.

A description will now be made of measuring a Force-Curve for determining surface adhesion. Here, the term "surface adhesion" means an adhesive force between a material making up the sample surface and a material to be formed on the sample surface. First, the switch 15 is opened and the switch 16 is closed in the control circuit 70 to open the feedback loop. Then, the reference voltage applied to the differential amplifier 10 is set to 0 V so that the output voltage of the differential amplifier 10 becomes 0 V. As a result, the output of the adder 13 holds the voltage that has been developed before the feedback loop is opened. In other words, the relative distance between the surface of the measured sample 3 and the probe 2 at the distal end of the cantilever 1 is fixed. Under this condition, the Z-driving triangular wave voltage is applied to the Z-electrode of the piezoelectric element 6 from the computer 71 through the D/A converter 74, the input terminal T2 and the high-voltage amplifier 14b. Based on the Z-driving triangular wave voltage applied to the piezoelectric element 6 and the output signal of the photodiode detector 5 at this time, the Force-Curve relating to one measuring point on the surface of the measured sample is obtained. A method of calculating the surface adhesion from the Force-Curve is similar to the conventional method described above by referring to FIGS. 22A to 22G.

Figure 2:
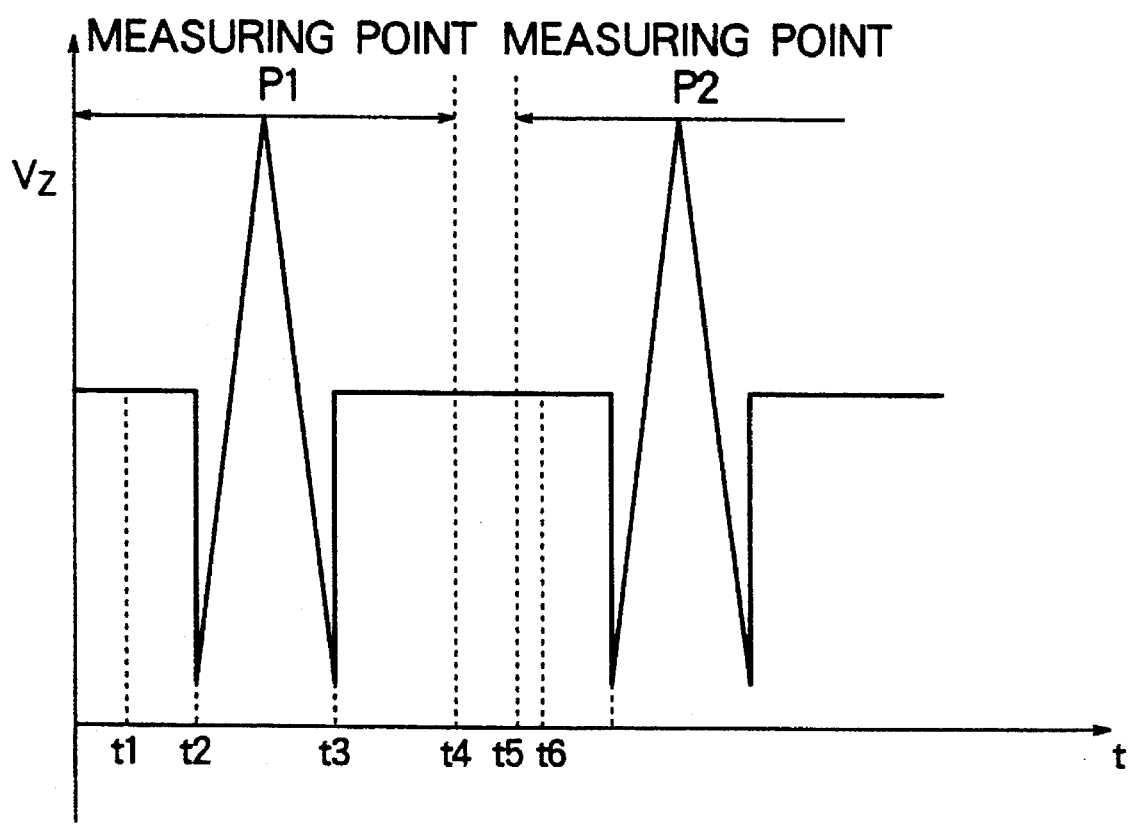
FIG. 2 is a timing chart showing operation of Embodiment 1.

With the adhesion measuring method according to the present invention, measurement of the image data of surface irregularities and measurement of the Force-Curve are carried out for all of a plurality of measuring points on the surface of the measured sample 3. Therefore, the timed relationship between the operation of measuring the image data of surface irregularities and the operation of measuring the Force-Curve, particularly, the timing at which the feedback loop is opened and closed, is important. FIG. 2 shows a timing chart for measurement in Embodiment 1. In FIG. 2, the vertical axis represents the voltage Vz applied to the Z-electrode of the piezoelectric element 15, and the horizontal axis represents time t.

First, under the condition in which the feedback loop is closed to keep the interatomic force between the probe 2 of the cantilever 1 and the measured sample 3 constant, the first measuring point P1 on the surface of the measured sample 3 is moved to a position below the probe 2. Then, image data of surface irregularities is measured at the time t1 and the measured data is stored in the RAM disk 72. After that, the feedback loop is opened at the time t2, and the Z-driving triangular wave voltage having a frequency of 20 Hz and an amplitude of ±160 V, for example, is applied to the piezoelectric element 6 to carry out measurement of the Force-Curve. At this time, the sample is moved over a range of ±320 V in the Z-direction. After the completion of measurement of the Force-Curve, the feedback loop is closed at the time t3 and the computer 71 calculates surface adhesion from the measured Force-Curve, the calculated result being stored in the RAM disk 72. Note that, as described before in connection with the prior art, the surface adhesion is calculated by multiplying the spring constant of the cantilever 1 by the flexure of the cantilever 1. After the surface adhesion has been calculated, the computer 71 generates the measured sample 3 causing signals to move in the X- and Y-directions during a period between the time t4 and t5 so that the second measuring point P2 on the measured sample 3 is positioned below the probe 2. Subsequently, image data of surface irregularities for the second measuring point P2 is measured at the time t6.

Likewise, the above sequence is repeatedly carried out for all of the measuring points set within a surface region of the measured sample 3 to be observed, e.g., for each of 64× 64 points or 128×128 points. Then, the computer 71 forms an image of surface irregularities for the observed region from the image data of surface irregularities obtained at all of the measuring points, and also forms an image of the surface adhesion distribution from the values of the surface adhesion obtained at all of the measuring points. Since the image of surface irregularities and the image of surface adhesion distribution are formed based on the data that are taken in from the same measuring point substantially at the same time, the surface condition of the measured sample 3 can be accurately grasped by comparing the two images with each other.

Figure 3:
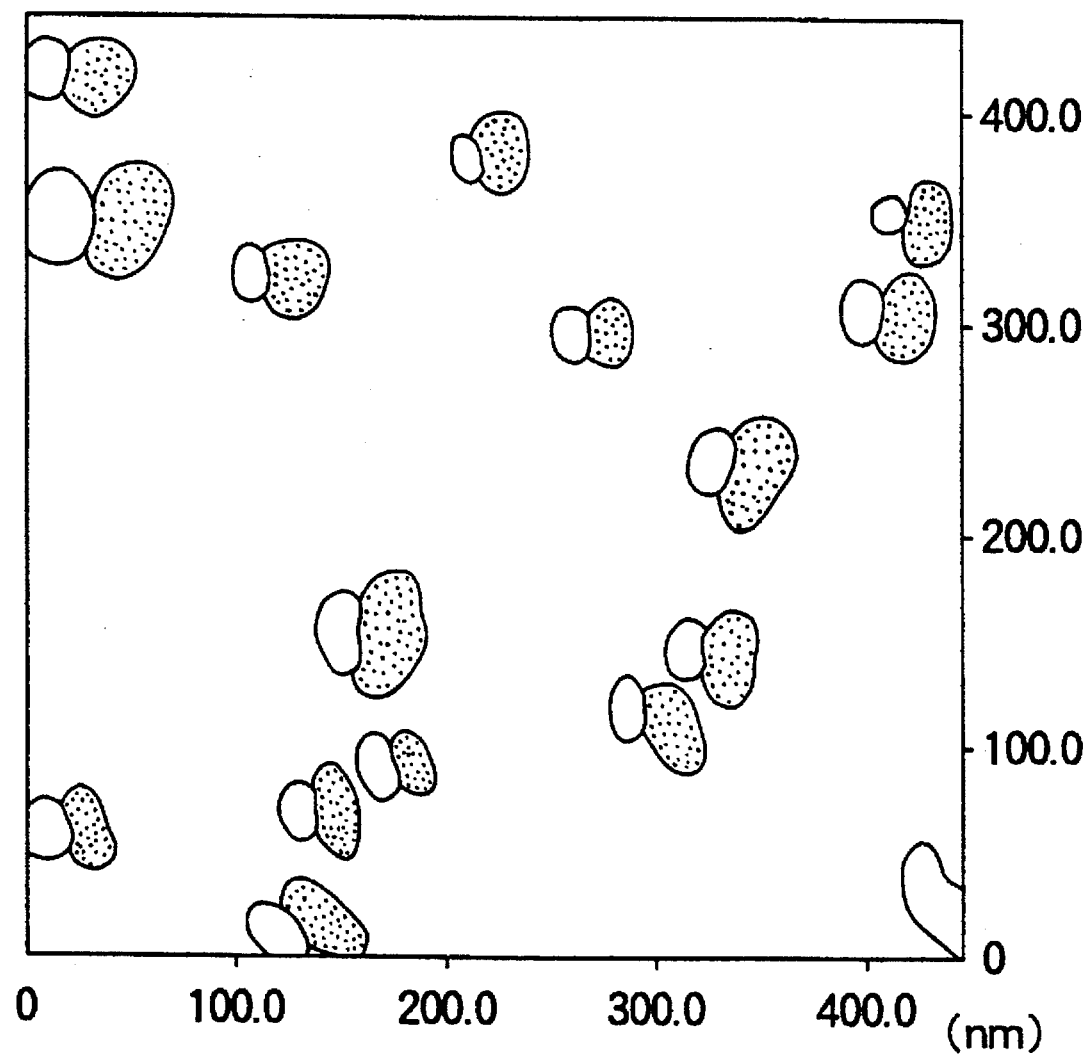
FIG. 3 is a diagram showing an image of surface irregularities of an InP semiconductor substrate produced by Embodiment 1.
Figure 4A:
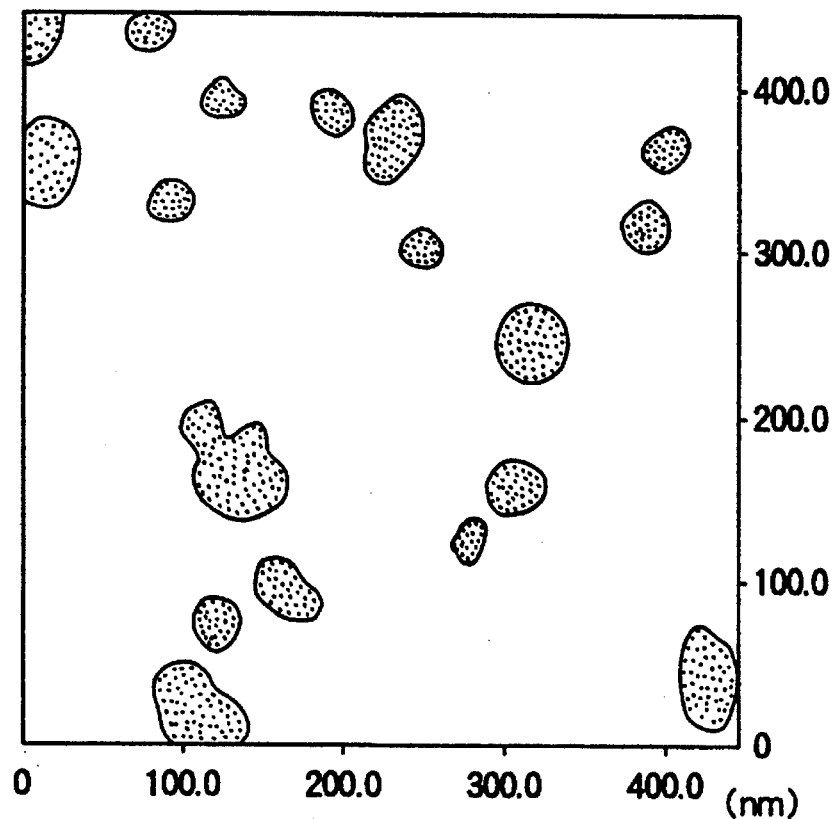
FIGS. 4A and 4B are a diagram showing an image of surface adhesion distribution of an InP semiconductor substrate produced by Embodiment 1 and a diagram showing a scale of the distribution, respectively.
Figure 4B:
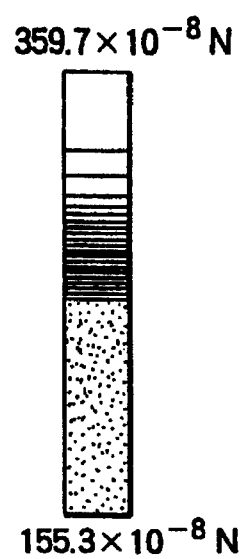

FIGS. 3 and 4A show respectively an image of surface irregularities and an image of surface adhesion distribution of an InP semiconductor substrate produced by the method of this Embodiment 1. The probe 2 employed here is made of silicon nitride ($Si_3N_4$). The InP semiconductor substrate measured has been subjected to HBr treatment and water washing, and residual particles exist on the substrate surface. The observed region is 440 nm×440 nm and the number of measuring points is 64×64. The surface adhesion at each point can be determined from the image of surface adhesion distribution of FIG. 4A by referring to a scale shown in FIG. 4B. The maximum height of the residual particles is 7 nm, and the surface tension has a minimum value of $155.3×10^{-8}N$ and a maximum value of $359.7×10^{-8}N$. From comparison between the image of surface irregularities and the image of surface adhesion distribution, it is seen that the surface adhesion in areas where residual particles exist is about half that in areas where no residual particles exist.

Figure 5:
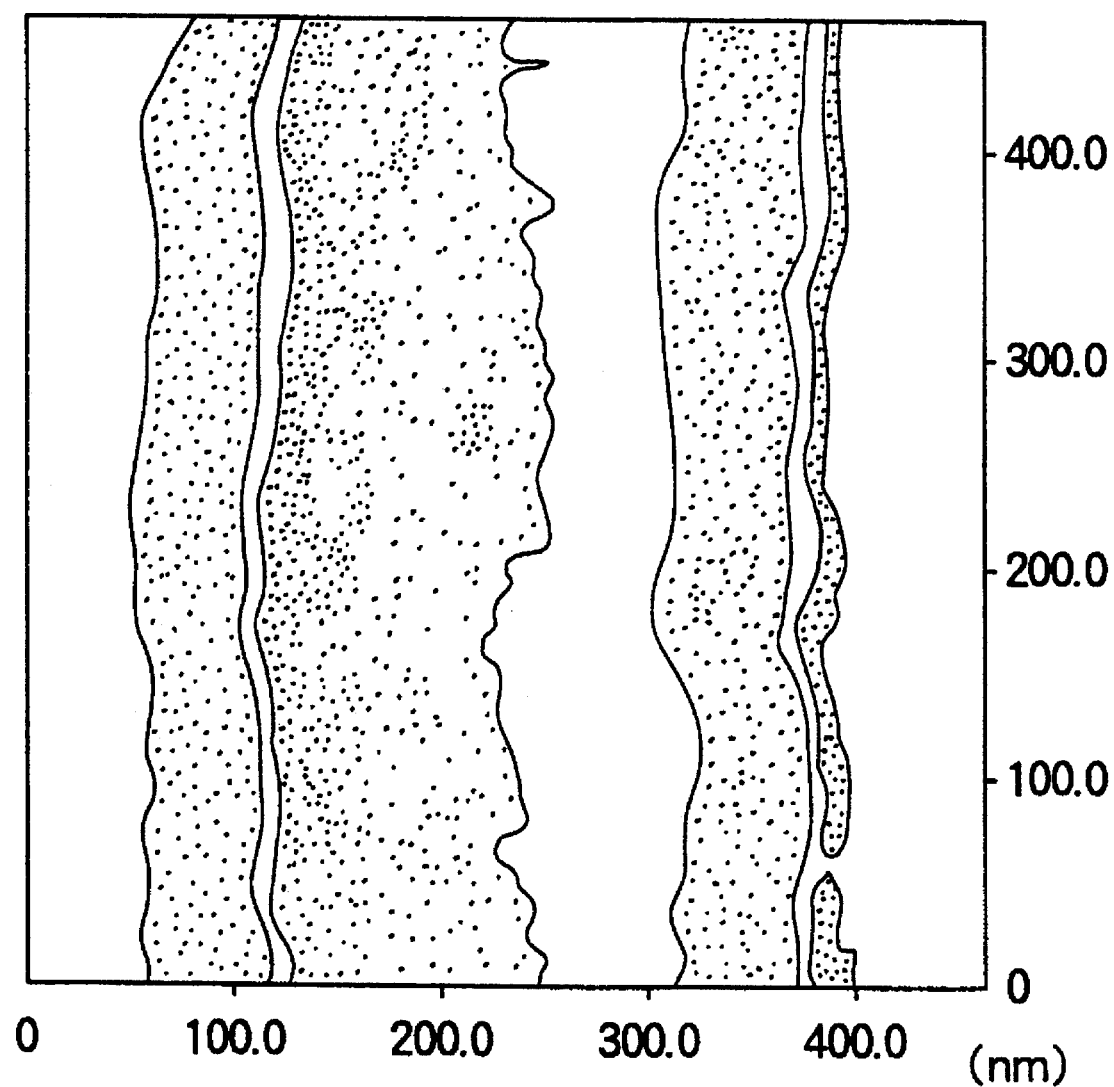
FIG. 5 is a diagram showing an image of surface irregularities of an InGaAsP semiconductor substrate produced by Embodiment 1.
Figure 6A:
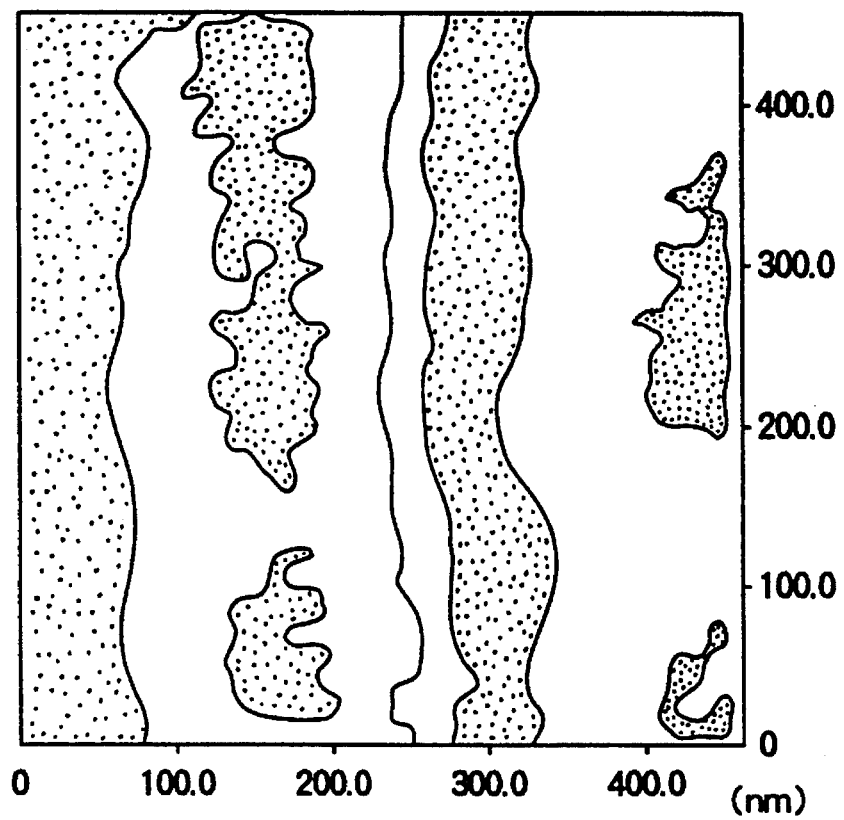
FIGS. 6A and 6B are a diagram showing an image of surface adhesion distribution of the InGaAsP semiconductor substrate produced by Embodiment 1 and a diagram showing a scale of the distribution, respectively.
Figure 6B:
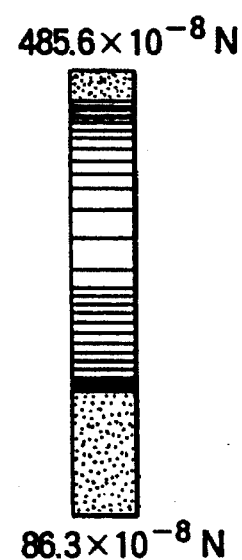

FIGS. 5 and 6A show respectively an image of surface irregularities and an image of surface adhesion distribution of a resist pattern on the surface of an InGaAsP semiconductor substrate produced by the method of Embodiment 1. The probe 2 employed here is also made of silicon nitride ($Si_3N_4$). The resist pattern is a pattern having a thickness of 90 nm with lines and spaces being each 100 nm wide. The observed region is 440 nm×440 nm and the number of measuring points is 64×64. The surface adhesion at each point can be determined from the image of surface adhesion distribution of FIG. 6A by referring to a scale shown in FIG. 6B. The surface tension has a minimum value of $86.3×10^{-8}N$ and a maximum value of $485.6×10^{-8}N$. For this sample, it is seen that the surface adhesion in resist areas is 5 to 6 times as strong as that in ground areas of the InGaAsP semiconductor substrate. Thus, the adhesion of the sample surface is different depending on the material of the sample.

Embodiment 2

In Embodiment 1, the adhesion is calculated immediately after measurement of the Force-Curve at each measuring point, and the calculated result is stored in the RAM disk 72. However, the time required to calculate the adhesion is about 50 msec for each measuring point. Hence, if the adhesion is calculated for all of the measuring points of 64×64, for example, the total time of about 3 minutes and 30 seconds is required only for calculating the adhesion. When measuring an image of surface irregularities, a shorter period of time required for one sequence of measurement is more advantageous in preventing adverse effects such as drift of the sample. In this Embodiment 2, therefore, after the Force-Curve is measured at each measuring point on the surface of the measured sample 3, the adhesion is not calculated immediately, but the measured data of the Force-Curve is all once stored in the RAM disk 72. Then, after the measurement is finished for all of the measuring points, the adhesion is calculated for all of the measuring points collectively.

Figure 7:
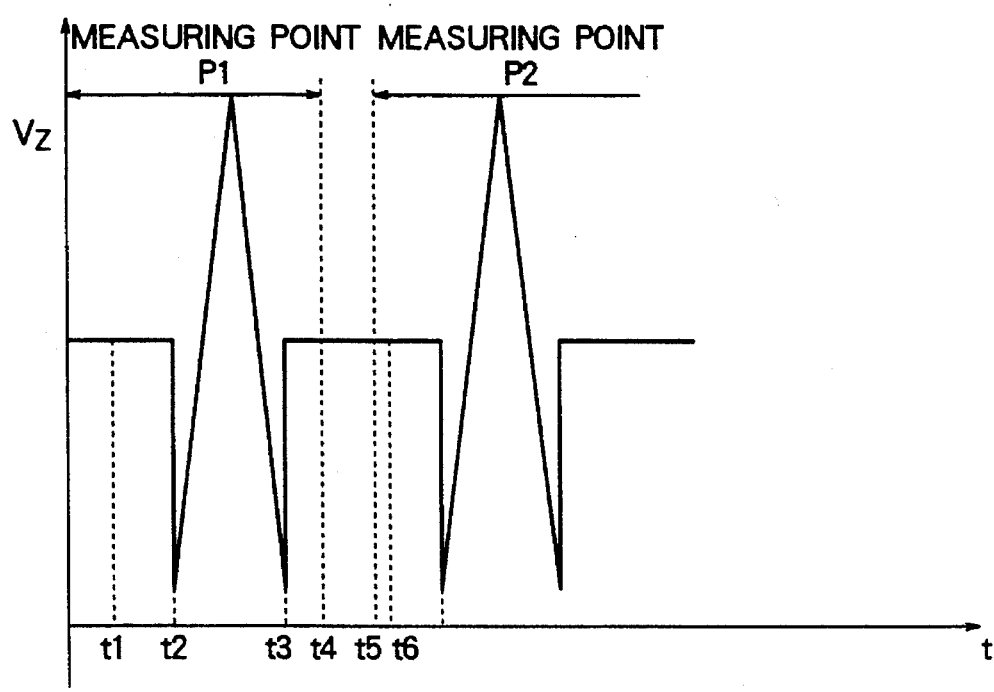
FIG. 7 is a timing chart showing operation of Embodiment 2 of the present invention.

FIG. 7 shows a timing chart for measurement in Embodiment 2. First, under the condition in which the feedback loop is closed to keep the interatomic force between the probe 2 of the cantilever 1 and the measured sample 3 constant, the first measuring point P1 on the surface of the measured sample 3 is moved to a position below the probe 2. Then, image data of surface irregularities is measured at the time t1 and the measured data is stored in the RAM disk 72. After that, the feedback loop is opened at the time t2, and the Z-driving triangular wave voltage having a frequency of 20 Hz and an amplitude of 340 V, for example, is applied to the piezoelectric element 6 to carry out measurement of the Force-Curve. After the completion of measurement of the Force-Curve, the feedback loop is closed at the time t3 and the computer 71 stores the measured data of the Force-Curve in the RAM disk 72. Following storage of the measured data of the Force-Curve, the computer 71 moves the measured sample 3 in the X- and Y-directions during a period between the time t4 and t5 so that the next second measuring point P2 on the measured sample 3 is positioned below the probe 2. Subsequently, image data of surface irregularities for the second measuring point P2 is measured at the time t6.

Likewise, the above sequence is repeatedly carried out fox all of measuring points set within a surface region of the measured sample 3 to be observed, e.g., for each of 64×64 points or 128×128 points. When the measurement has been completed for all of the measuring points, the computer 71 reads out the measured data of the Force-Curve for each of the measuring points stored in the RAM disk 72, and calculates a surface adhesion at each measuring point from the measured data. Then, the computer 71 forms an image of surface adhesion distribution from the calculated values of the surface adhesion, and also forms an image of surface irregularities for the observed region from the image data of surface irregularities obtained at all of the measuring points.

Embodiment 3

When measuring the Force-Curve at each measuring point in Embodiment 1, only one cycle of the Z-driving triangular wave is applied to the cylindrical piezoelectric element 6. However, in the case of determining the surface adhesion from the Force-Curve in only one cycle, there is a fear that the surface adhesion may not be determined because of the presence of disturbances such as vibration, sound and electrical noise. In this Embodiment 3, therefore, the Z-driving triangular wave voltage is applied to the piezoelectric element 5 in two cycles successively at each measuring point. This enables the surface adhesion to be more reliably determined. Note that the number of cycles of the applied Z-driving triangular wave voltage is not limited to two, but may be three or more in succession.

Figure 8:
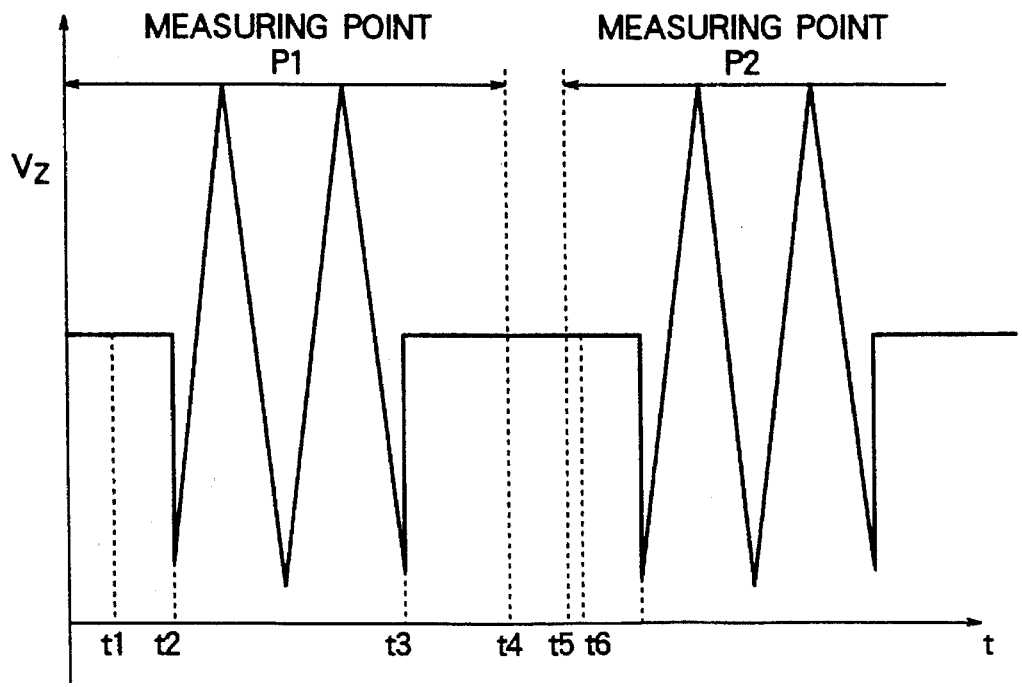
FIG. 8 is a timing chart showing operation of Embodiment 3 of the present invention.

FIG. 8 shows a timing chart for measurement in Embodiment 3. First, under the condition in which the feedback loop is closed to keep the interatomic force between the probe 2 of the cantilever 1 and the measured sample 3 constant, the first measuring point P1 on the surface of the measured sample 3 is moved to a position below the probe 2. Then, image data of surface irregularities is measured at the time t1 and the measured data is stored in the RAM disk 72. After that, the feedback loop is opened at the time t2, and the Z-driving triangular wave voltage having a frequency of 20 Hz and an amplitude of ±160 V, for example, is applied to the piezoelectric element 6 in two cycles to carry out measurement of the Force-Curve. After the completion of measurement of the Force-Curve, the feedback loop is closed at the time t3 and the computer 71 calculates a surface adhesion from each of the two measured Force-Curves. The calculated results are averaged and the average value is stored in the RAM disk 72. After the surface adhesion has been calculated, the computer 71 moves the measured sample 3 in the X- and Y-directions during a-period between the time t4 and t5 so that the next, i.e., second, measuring point P2 on the measured sample 3 is positioned below the probe 2. Subsequently, image data of surface irregularities for the second measuring point P2 is measured at the time t6.

Likewise, the above sequence is repeatedly carried out for all of the measuring points in a set within a surface region of the measured sample 3 to be observed, e.g., for each of 64×64 points or 128×128 points. Then, the computer 71 forms an image of surface irregularities and an image of the surface adhesion distribution from the image data of surface irregularities and the calculated values of the surface adhesion, respectively, which are obtained at all of the measuring Points.

Embodiment 4

In above Embodiments 1 to 3, image data of surface irregularities are first measured after moving the measured sample 3 so that a new measuring point is positioned below the probe 2. Taking into account stability of the AFM operation, however, if image data of surface irregularities is read immediately after moving the sample 3, there is a fear of reducing reliability of the data. In this Embodiment 4, therefore, after moving the sample 3, the Focus-Curve is first measured and the image data of surface irregularities is then measured.

Figure 9:
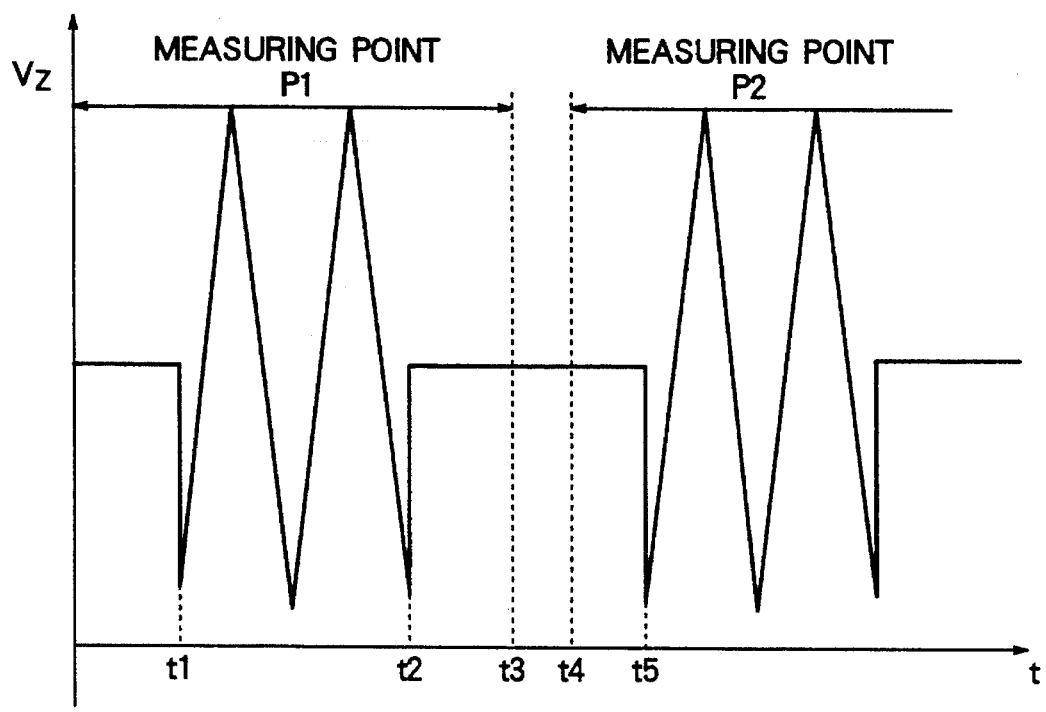
FIG. 9 is a timing chart showing operation of Embodiment 4 of the present invention.

FIG. 9 shows a timing chart for measurement in Embodiment 4. First, under the condition in which the feedback loop is closed to keep the interatomic force between the probe 2 of the cantilever 1 and the measured sample 3 constant, the first measuring point P1 on the surface of the measured sample 3 is moved to a position below the probe 2. Then, the feedback loop is opened at the time t1, and the Z-driving triangular wave voltage having a frequency of 20 Hz and an amplitude of ±160 V, for example, is applied to the piezoelectric element 6 in two cycles to carry out measurement of the Force-Curve. After the completion of measurement of the Force-Curve, the feedback loop is closed at the time t2 and the computer 71 calculates a surface adhesion from each of the two measured Force-Curves. The calculated results are averaged and the average value is stored in the RAM disk 72. After the surface adhesion has been calculated, the computer 71 measures image data of surface irregularities at the time t3 and stores the measured data in the RAM disk 72. After that, the computer 71 moves the measured sample 3 in the X- and Y-directions during a period between the time t4 and t5 so that the second measuring point P2 on the measured sample 3 is positioned below the probe 2. Subsequently, the feedback loop is opened to carry out measurement of the Force-Curve for the second measuring point P2.

Likewise, the above sequence is repeatedly carried out for all of measuring points set within a surface region of the measured sample 3 to be observed, e.g., for each of 64×64 points or 128×128 points. Then, the computer 71 forms an image of surface irregularities and an image of surface adhesion distribution from the image data of surface irregularities and the calculated values of the surface adhesion, respectively, which are obtained at all of the measuring points.

Embodiment 5

In this Embodiment, when the surface adhesion cannot be calculated in measurement of the Force-Curve at any measuring point even with the Z-driving triangular wave voltage applied to the piezoelectric element 6 in two cycles, the measured sample 3 is not moved to the next measuring point, but the Z-driving triangular wave voltage is applied again to the piezoelectric element 6 at the same measuring point. This results in higher reliability of the surface adhesion data.

Figure 10:
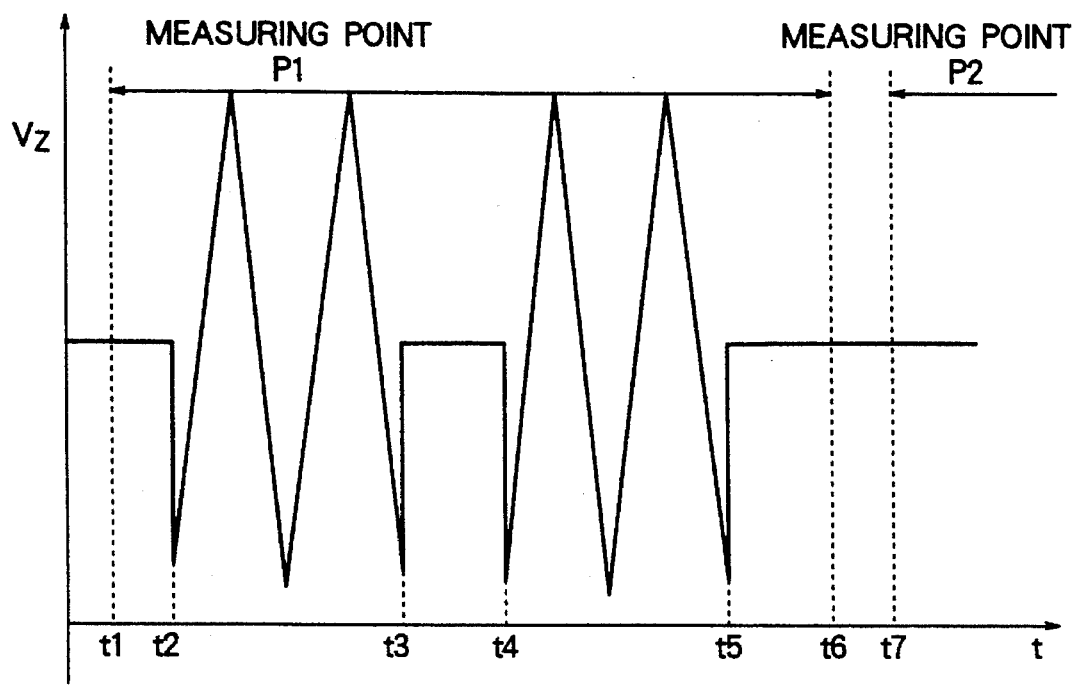
FIG. 10 is a timing chart showing operation of Embodiment 5 of the present invention.

FIG. 10 shows a timing chart for measurement in Embodiment 5. First, under the condition in which the feedback loop is closed to keep the interatomic force between the probe 2 of the cantilever 1 and the measured sample 3 constant, the first measuring point P1 on the surface of the measured sample 3 is moved to a position below the probe 2. Then, image data of surface irregularities is measured at the time t1 and the measured data is stored in the RAM disk 72. After that, the feedback loop is opened at the time t2, and the Z-driving triangular wave voltage having a frequency of 20

Hz and an amplitude of ±160 V, for example, is applied to the piezoelectric element 6 in two cycles to carry out measurement of the Force-Curve. After the completion of measurement of the Force-Curve, the feedback loop is closed at the time t3 and the computer 71 calculates a surface adhesion from each of the two measured Force-Curves. The calculated results are averaged and the average value is stored in the RAM disk 72. When the surface adhesion cannot be calculated at this time, the feedback loop is opened at the time t4 and the Z-driving triangular wave voltage is applied to the piezoelectric element 5 in two cycles to carry out measurement of the Force-Curve again. Then, the feedback loop is closed at the time t5 and the computer 71 calculates a surface adhesion from each of the two measured Force-Curves. The calculated results are averaged and the average value is stored in the RAM disk 72. After the surface adhesion has been calculated, the computer 71 moves the measured sample 3 in the X- and Y-directions during a period between the time t6 and t7 so that the next second measuring point P2 on the measured sample 3 is positioned below the probe 2. Subsequently, image data of surface irregularities for the second measuring point F2 is measured.

Likewise, the above sequence is repeatedly carried out for all of measuring points set within a surface region of the measured sample 3 to be observed, e.g., for each of 64×64 points or 128×128 points. Then, the computer 71 forms an image of surface irregularities and an image of surface adhesion distribution from the image data of surface irregularities and the calculated values of the surface adhesion, respectively, which are obtained at all of the measuring points.

Embodiment 6

As described in connection with Embodiment 1, in measurement of the Force-Curve, the feedback loop is once opened and the reference voltage applied to the differential amplifier 10 in the control circuit 70 is set to 0 V so that the relative distance between the surface of the measured sample 3 and the probe 2 at the distal end of the cantilever 1 is fixed. On the contrary, this Embodiment 6 is arranged to control measurement of the Force-Curve so that an absolute position of the surface of the measured sample 3 with respect to a tunnel unit base is kept fixed.

Figure 11:
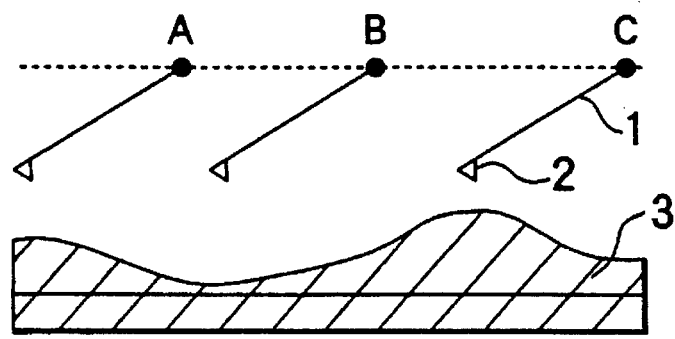
FIG. 11 is a diagram showing the operating principle of Embodiment 6 of the present invention.
Figure 12:
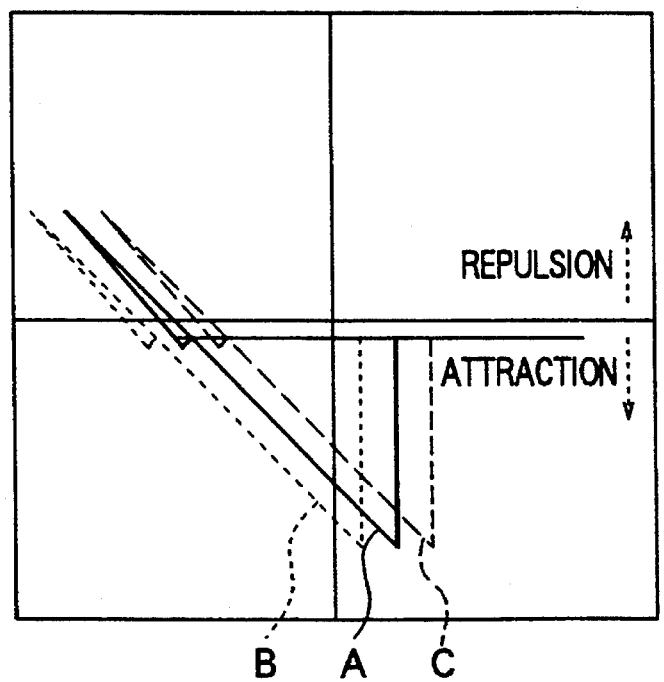
FIG. 12 is a graph showing Force-Curves measured at measuring points A to C in FIG. 11.

When the feedback loop is opened to fix the Z-directional control voltage, absolute position of the surface of the measured sample 3 with respect to the tunnel unit base is always kept fixed. This means that, as shown in FIG. 11, the relative distance between the probe 2 of the cantilever 1 and the surface of the measured sample 3 is varied depending on measuring points A, B and C. In this case, measuring the Force-Curve at each of the measuring points A, B and C provides three Force-Curves which are the same in shape and size, but shifted along the horizontal axis (in the direction of Z-displacement) from each other. Accordingly, the same calculated result is obtained even if the surface adhesion is calculated from any of the Force-Curves for the measuring points A, B and C. In other words, a shift of the Force-Curve along the horizontal axis has to no effect on calculation of the adhesion between the probe 2 and the surface of the measured sample 3.

Operation of measuring the Force-Curve in Embodiment 6 will be described with reference to the circuit of FIG. 1. A switch 17 in the control circuit 70 is opened to open the feedback loop, and a switch 18 is closed, causing the integrating amplification circuit 11 to produce a constant voltage. An absolute position of the surface of the measured sample 3 with respect to the tunnel unit base is thereby kept fixed. Next, after opening the switch 15 and closing the switch 16, the Z-driving triangular wave voltage for the piezoelectric element 6 is applied to the differential amplifier 10 through the D/A converter 76 instead of the reference voltage. The Z-driving triangular wave voltage is applied to the Z-electrode of the piezoelectric element 6 through the differential amplifier 10, the proportional amplification circuit 12, the adder 13 and the high-voltage amplifier 14a for measurement of the Force-Curve.

Figure 13:
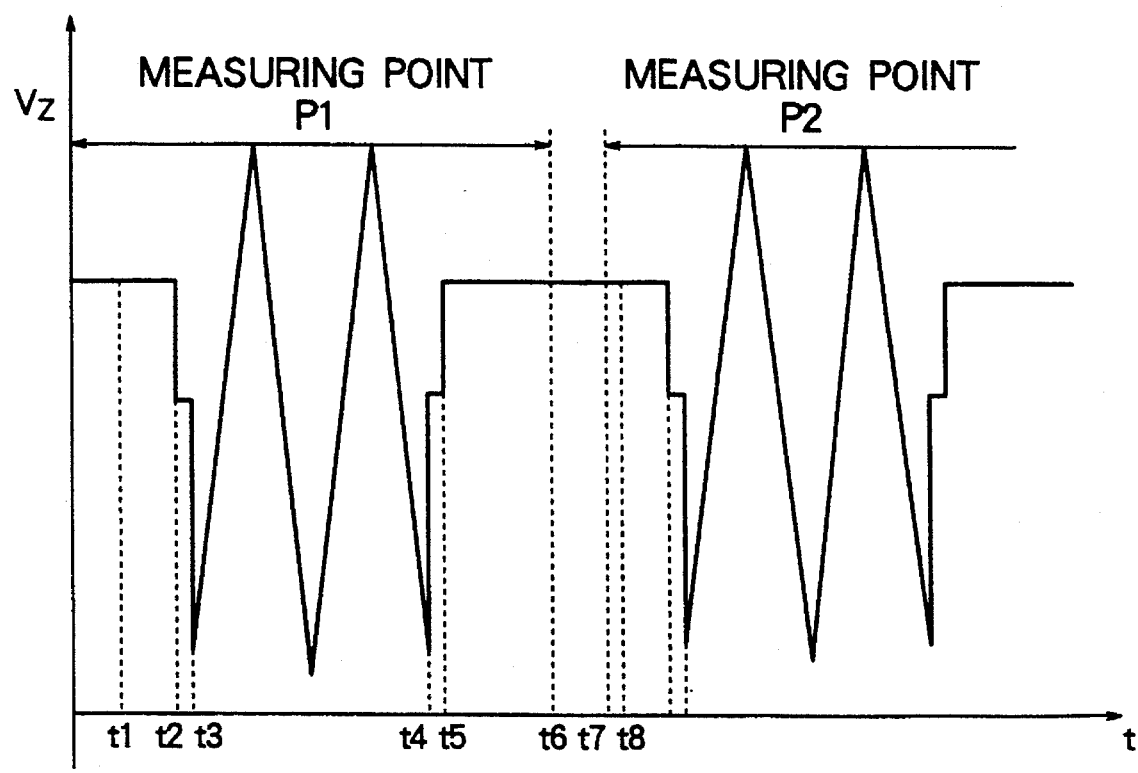
FIG. 13 s a timing chart showing operation of Embodiment 6 of the present invention.

FIG. 13 shows a timing chart for measurement in Embodiment 6. First, under the condition in which the feedback loop is closed to keep the interatomic force between the probe 2 of the cantilever 1 and the measured sample 3 constant, the first measuring point P1 on the surface of the measured sample 3 is moved to a position below the probe 2. Then, image data of surface irregularities is measured at the time t1 and the measured data is stored in the RAM disk 72. After that, the feedback loop is opened at the time t2, and the Z-directional control voltage is fixed to 10 V, for example. Then, the Z-driving triangular wave voltage having a frequency of 20 Hz and an amplitude of 340 V, for example, is applied at the time t3 to the piezoelectric element 6 in two cycles to carry out measurement of the Force-Curve. After the completion of measurement of the Force-Curve, the Z-directional control voltage is fixed to 10 V again at the time t4. The feedback loop is then closed at the time t5 and the computer 71 calculates a surface adhesion from each of the two measured Force-Curves. The calculated results are averaged and the average value is stored in the RAM disk 72. After the surface adhesion has been calculated, the computer 71 moves the measured sample 3 in the X- and Y-directions during a period between the time t6 and t7 so that the next second measuring point P2 on the measured sample 3 is positioned below the probe 2. Subsequently, image data of surface irregularities for the second measuring point P2 is measured at the time t8.

Likewise, the above sequence is repeatedly carried out for all of the measuring points in a set within a surface region of the measured sample 3 to be observed, e.g., for each of 64× 64 points or 128×128 points. Then, the computer 71 forms an image of surface irregularities and an image of surface adhesion distribution from the image data of surface irregularities and the calculated values of the surface adhesion, respectively, which are obtained at all of the measuring points.

Embodiment 7

While a relatively small slice is attached as the measured sample 3 to the cylindrical piezoelectric element 6 in above Embodiments 1 to 6, a semiconductor wafer, for example, may be used as the measured sample instead of the slice. In this case, the surface measuring method of the present invention can be applied as an on-line measuring method for use with a semiconductor device manufacturing process.

Figure 14:
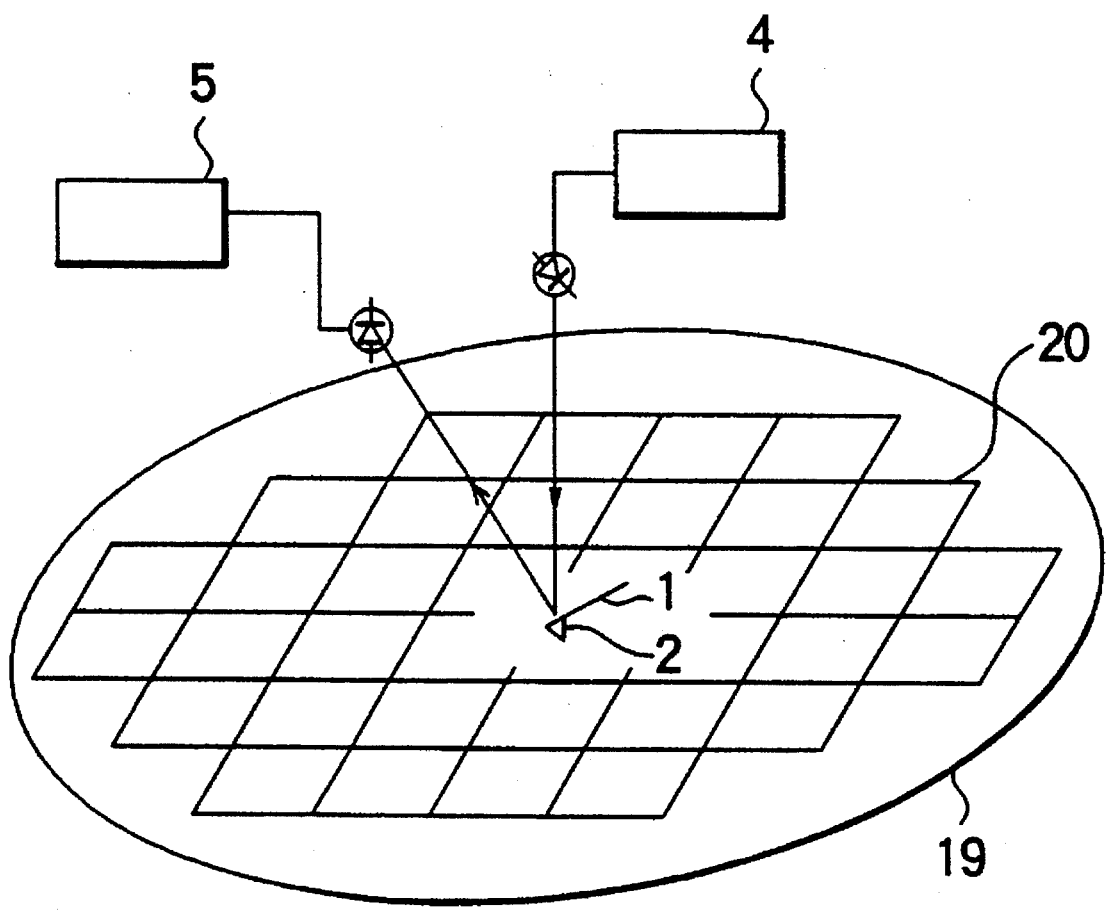
FIG. 14 is a diagram showing an inspection method according to Embodiment 7 of the present invention.

In this Embodiment 7, as shown in FIG. 14, during the process of manufacturing a semiconductor device, an image of the surface adhesion distribution of the surface of a semiconductor element 20 patterned on a semiconductor wafer 19 is measured to inspect whether a surface adhesion greater than a predetermined value is obtained. An image of surface adhesion distribution is measured by moving the semiconductor element 20 close to a probe 2 at the distal end of a cantilever 1 of an adhesion measuring apparatus. This adhesion measuring apparatus is arranged, as with that shown in FIG. 1, such that a laser beam from a semiconductor laser unit 4 irradiates to the cantilever 1 and a shift in position of a reflected beam from the cantilever 1 is read by the photodiode detector 5.

Figure 15:
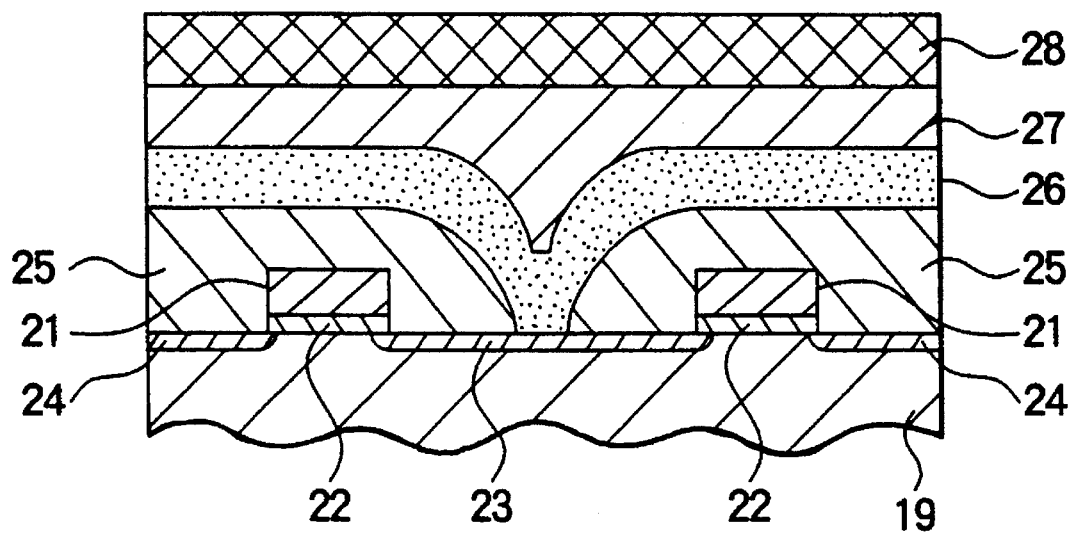
FIG. 15 a sectional view showing a semiconductor device inspected by Embodiment 7.

Here, the semiconductor element 20 has a sectional structure as shown in FIG. 15, by way of example. A transistor comprising polysilicon gates 21, gate insulating films 22, a source area 23 and a drain area 24 is located on a semiconductor wafer 19. On this transistor, there are an interlayer insulating film 25 and a metallic wiring layer 26 connected to the source area 23. Furthermore, a second interlayer insulating film 27 is disposed on the metallic wiring layer 26, and a second metallic wiring layer 28 is disposed on the second interlayer insulating film 27.

Figure 16:
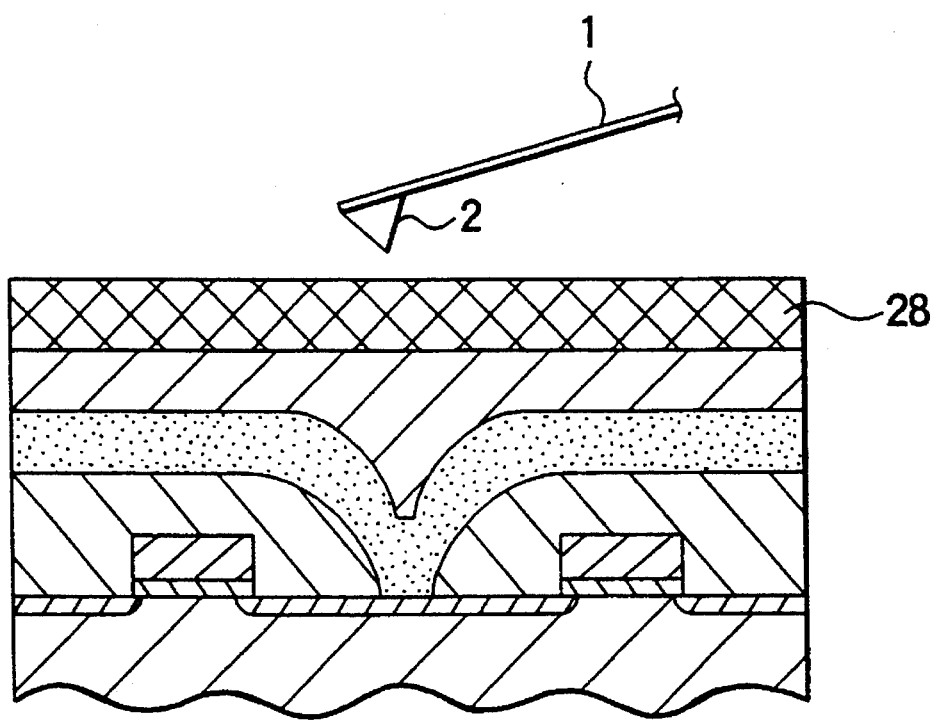
FIG. 16 is a sectional view showing the semiconductor device under inspection by Embodiment 7.

In a subsequent step, the second metallic wiring layer 28 is patterned to form a second wiring pattern. Prior to that step, the surface adhesion of the second metallic wiring layer 28 is inspected as follows. First, as shown in FIG. 16, the cantilever 1 and the probe 2 of the adhesion measuring apparatus are moved close to the surface of the second metallic wiring layer 28 for measuring an image of surface adhesion distribution in accordance with any of the methods described above in Embodiments 1–6.

Figure 17:
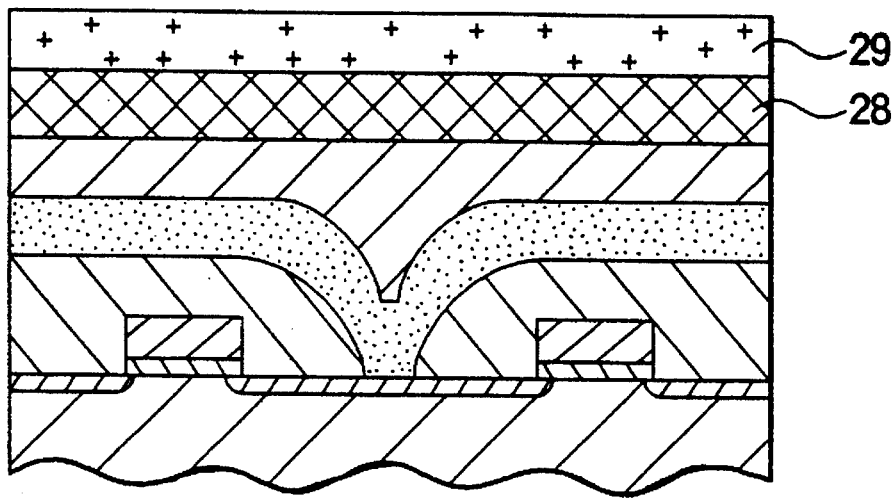
FIG. 17 is a sectional view showing the semiconductor device which has been subjected to a next step after inspection by Embodiment 7.
Figure 18:
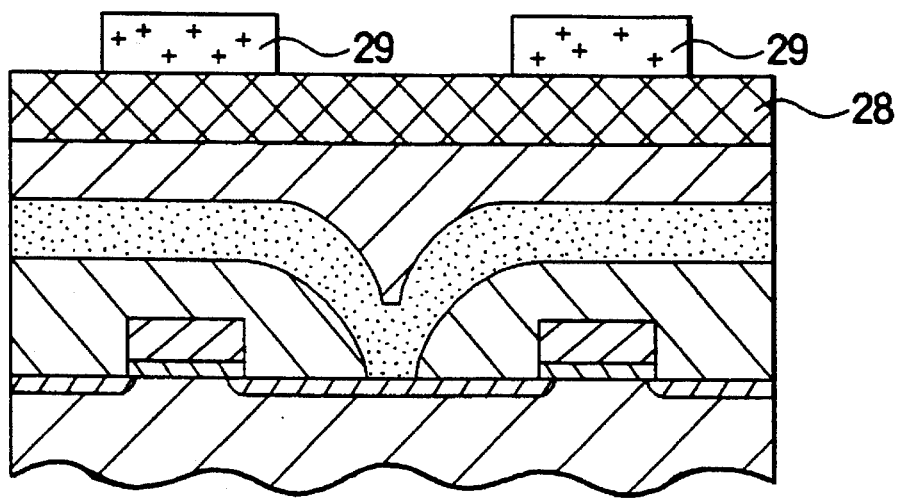
FIG. 18 is a sectional view showing the semiconductor device which has been subjected to a further step after inspection by Embodiment 7.
Figure 19:
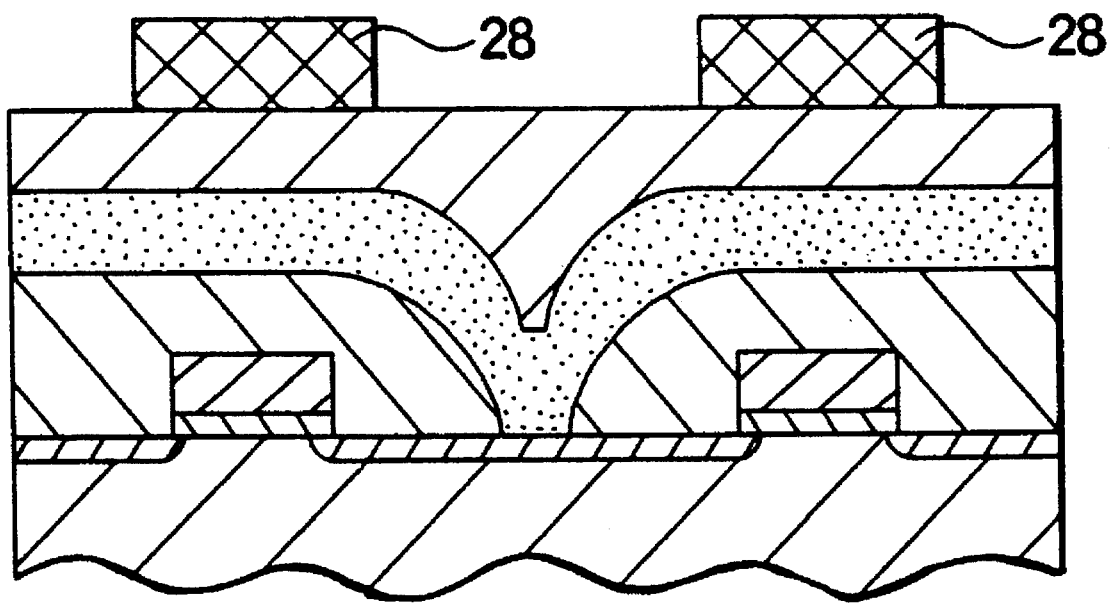
FIG. 19 is a sectional view showing the semiconductor device which has been subjected to a still further step after inspection by Embodiment 7.
Figure 20:
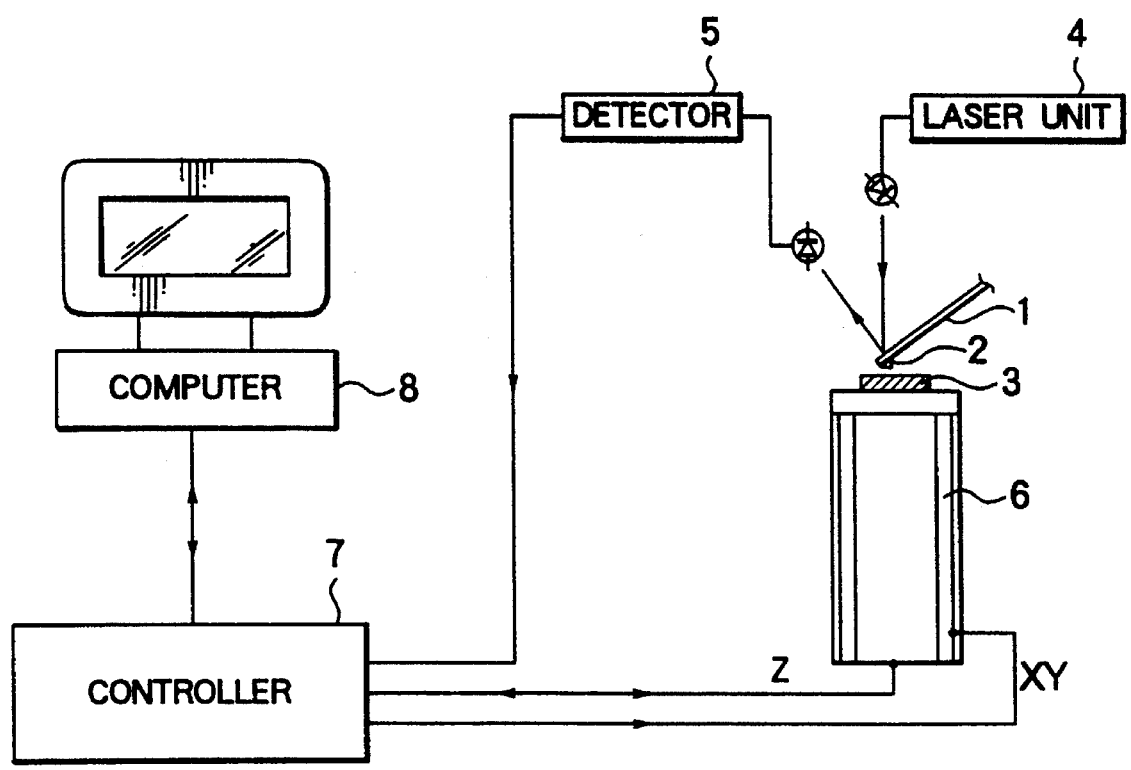
FIG. 20 is a block diagram of a conventional interatomic force microscope.
Figure 21:
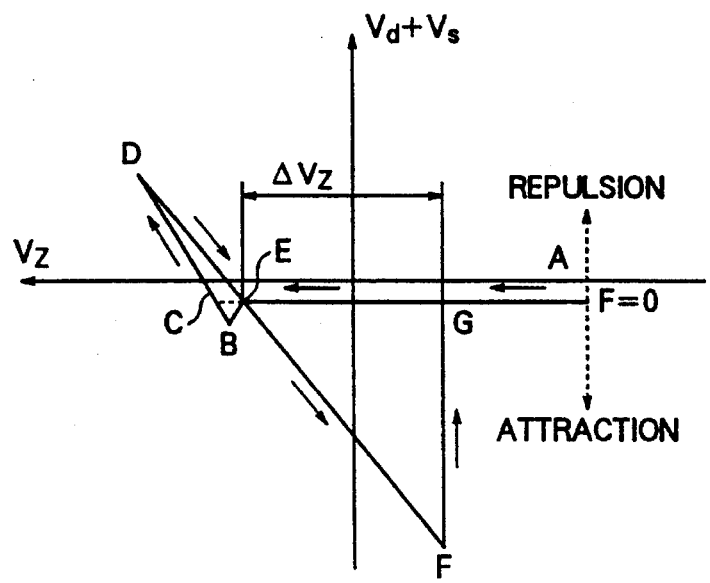
FIG. 21 is a graph showing a Force-Curve measured by using the conventional interatomic force microscope.
Figure 22A:
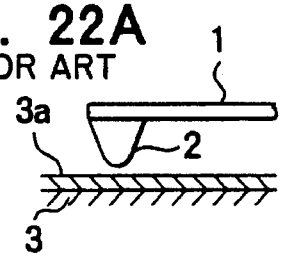
FIGS. 22A to 22G are side views of a cantilever at points A to G in FIG. 21, respectively.
Figure 22B:
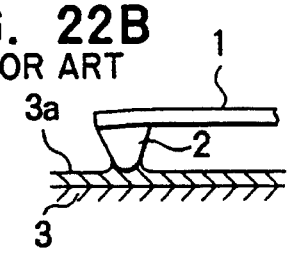
Figure 22C:
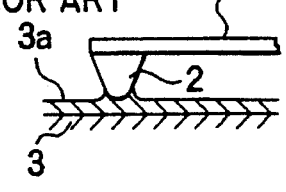
Figure 22D:
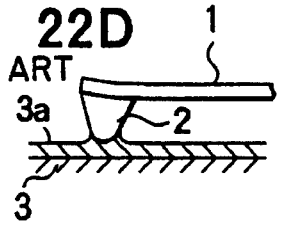
Figure 22E:
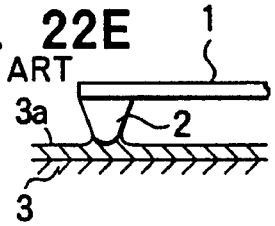
Figure 22F:
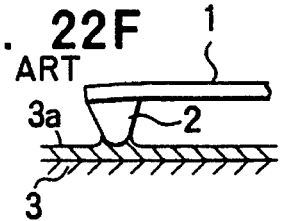
Figure 22G:
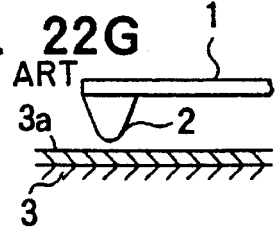
Figure 23:
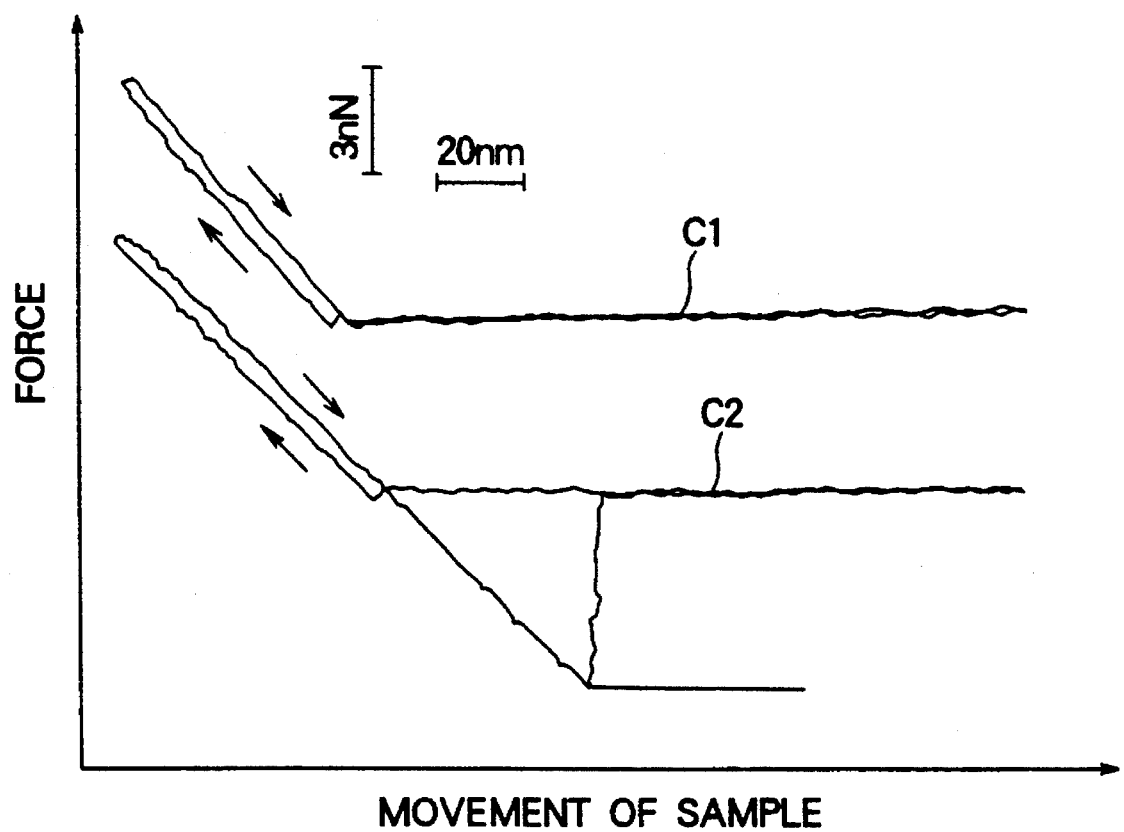
FIG. 23 is a graph showing typical Force-Curves measured by using the conventional interatomic force microscope.

If it is determined from the result of measurement that a surface adhesion greater than a predetermined value is obtained, the process goes to the next step. Specifically, a photoresist 29 is applied over the second metallic wiring layer 28 as shown in FIG. 17, and the semiconductor element is subjected to exposure of the pattern of the photoresist 29 as shown in FIG. 18. After that, as shown in FIG. 19, the second metallic wiring layer 28 is patterned with the photoresist 29 serving as a mask, followed by moving the photoresist 29. As a result, the second wiring pattern is formed.

On the other hand, if it is determined from the result of measuring the image of surface adhesion distribution that a surface adhesion greater than the predetermined value is not obtained, the semiconductor wafer is judged to have failed in the stage of FIG. 15 and is removed from the production line. This is because, if the surface adhesion greater than the predetermined value is not obtained, delamination between the second metallic wiring layer 28 and the photoresist 29 thereon will occur.

With the above-described inspecting method, without actually forming the photoresist 29 on the second metallic wiring layer 28, it can be determined whether delamination between them will occur. Therefore, the semiconductor device can be manufactured highly efficiently. Likewise, it is also possible to measure an adhesion between the surface of a material of one of a substrate, an insulating film, a wiring layer, an electrode layer, and a resist layer making up a semiconductor device and a material to be next formed on the surface of the former material, thereby determining whether a surface adhesion greater than the predetermined value is obtained. Note that such an inspection step can be either incorporated as an on-line inspection in the production line of semiconductor devices, or conducted as an off-line step separate from the production line.

Embodiment 8

In each of above Embodiments, the cylindrical piezoelectric element 6 is used to scan and move the measured sample 3. However, the piezoelectric element 6 is not limited to a cylindrical type, and similar advantages can also be obtained by using a piezoelectric element of a tripod, laminated or tower type.

What is claimed is:

1. An adhesion measuring method comprising:

adjusting the spacing between (i) a probe located at a distal end of a cantilever and made of a material to be deposited on a sample surface and (ii) a sample surface at a first measuring point on the sample surface opposite the probe, thereby measuring a Force-Curve at the first measuring point on the sample surface;

measuring interatomic force at the first measuring point on the sample surface with the probe;

moving the probe sequentially to second, third, and additional positions opposite respective second, third, and additional measuring points on the sample surface and repeating, for each measuring point, the foregoing steps of measuring a Force-Curve and measuring interatomic force;

calculating adhesion between the sample surface and the material to be deposited on the sample surface at each of the measuring points from the respective measured Force-Curves;

forming a two-dimensional image of the adhesion for each of the measuring points on the sample surface, each adhesion being displayed in the image at a location corresponding to the respective measuring point; and forming a two-dimensional image of the interatomic force for each of the measuring points on sample surface, each interatomic force being displayed in the image at a location corresponding to the respective measuring point.

2. The adhesion measuring method according to claim 1 wherein the interatomic force is measured while the spacing between the probe and the sample surface is kept constant.

3. The adhesion measuring method according to claim 1 wherein, after measuring the inter-atomic force and a Force-Curve at the same measuring point, calculating adhesion for that measuring point from the measured Force-Curve before moving the probe to another measuring point.

4. The adhesion measuring method according to claim 1 including storing the measured Force-Curve for each measuring point and, after measuring Force-Curves at each of the measuring points, calculating adhesion for each measuring point from the stored Force-Curves.

5. The adhesion measuring method according to claim 1 including measuring the Force-Curve at least twice at each of the measuring points.

6. The adhesion measuring method according to claim 1 including sequentially measuring the Force-Curve and the interatomic force at each of the measuring points before moving to another measuring point.

7. The adhesion measuring method according to claim 1 including setting the spacing between the probe and the sample surface to a fixed spacing at each of the measuring points before measuring the Force-Curve at the respective measuring points.

* * * * *